US00PP28542P3

(12) United States Plant Patent
Kordes

(10) Patent No.: US PP28,542 P3
(45) Date of Patent: Oct. 24, 2017

(54) FLORIBUNDA ROSE PLANT NAMED 'KORFLUSAMEA'

(50) Latin Name: *Rosa hybrida*
Varietal Denomination: KORflusamea

(71) Applicant: W. Kordes Söhne Rosenschulen GmbH & Co. KG, Klein Offenseth-Sparrieshoop (DE)

(72) Inventor: Tim-Hermann Kordes, Klein Offenseth-Sparrieshoop (DE)

(73) Assignee: W. Kordes Söhne Rosenschulen GmbH & Co. KG, Klein Offenseth-Sparrieshoop (DE)

( * ) Notice: Subject to any disclaimer, the term of this patent is extended or adjusted under 35 U.S.C. 154(b) by 139 days.

(21) Appl. No.: 14/545,935

(22) Filed: Jul. 8, 2015

(65) Prior Publication Data

US 2016/0014940 P1 Jan. 14, 2016

Related U.S. Application Data

(60) Provisional application No. 61/998,920, filed on Jul. 11, 2014.

(51) Int. Cl.
*A01H 5/02* (2006.01)

(52) U.S. Cl.
USPC ..... Plt./145

(58) Field of Classification Search
USPC ..... Plt./101, 141, 145
See application file for complete search history.

(56) References Cited

PUBLICATIONS

Help Find Me: Roses, Clematis and Peonies website. Citation for Korflusamea. https://www.helpmefind.com/rose/l.php?l=2.71688.0. Accessed Jan. 12, 2017. 1 page.*

* cited by examiner

*Primary Examiner* — Susan McCormick Ewoldt
*Assistant Examiner* — Karen Redden
(74) *Attorney, Agent, or Firm* — Samuel R. McCoy, Jr.

(57) ABSTRACT

'KORflusamea' is a new and distinct variety of *Rosa hybrida* which is characterized by the combination of an upright growth habit, an abundance of large and very double-type flowers which are yellow in color and also attractive foliage with very good disease resistance. The new variety propagates successfully by grafting and by stem cuttings and has shown to be uniform and stable in the resulting generations from asexual propagation.

1 Drawing Sheet

Latin name of genus and species: The Latin name of the genus and species of the novel variety disclosed herein is *Rosa hybrida*.

Variety denomination: The inventive variety of *Rosa hybrida* disclosed herein has been given the variety denomination 'KORflusamea'.

BACKGROUND OF THE INVENTION

The present invention relates to a new and distinct *Rosa hybrida*, floribunda rose cultivar, which has been given the variety denomination of 'KORflusamea'. Its market class is PLT/141.

Parentage: The *Rosa hybrida* variety 'KORflusamea' is the result of a controlled cross-pollination breeding program carried out by the inventor in Offenseth-Sparrieshoop, Germany. The objective of the said breeding program was to create a new and distinct rose plant with unique qualities, such as:

1. Uniform growth and flowering;
2. Abundant attractive, recurrent flowers;
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORflusamea' from all other varieties known to the inventor.

'KORflusamea' is a seedling selection which resulted from the controlled pollination of two *Rosa hybrida* cultivars during the summer of 2001. Said cross-pollination was made between the seed parent, *Rosa hybrida* 'KORkinteral' (unpatented), and the pollen parent, *Rosa hybrida* 'INTERfluco' (unpatented).

As part of a rose development program, Tim-Hermann Kordes germinated seeds from the aforementioned hybridization during the winter of 2001 and conducted evaluations and observations on the resulting seedlings in a controlled environment in Offenseth-Sparrieshoop, Germany. The resulting seedlings exhibited distinctive physical and biological characteristics. The new rose plant was selected as a single plant in May of 2002 from the seedling beds due to its superior characteristics and asexually propagated for further evaluation. This new and distinctive rose variety was given the name 'KORflusamea'.

Asexual Reproduction: The first asexual propagation of 'KORflusamea' was done by budding in July of 2002 at the inventor's nursery in Offenseth-Sparrieshoop, Germany. These initial and other subsequent propagations conducted in controlled environments demonstrate that 'KORflusamea' reproduces true to type in successive generations of asexual reproduction.

SUMMARY OF THE INVENTION

The following characteristics have been repeatedly observed and represent the distinguishing characteristics of the new *Rosa hybrida* cultivar 'KORflusamea'. These traits, in combination, distinguish 'KORflusamea' as a new and distinct cultivar.

1. *Rosa hybrida* 'KORflusamea' exhibits an upright growth habit; and
2. *Rosa hybrida* 'KORflusamea' exhibits an abundance of flowers; and
3. *Rosa hybrida* 'KORflusamea' exhibits a very-double flower habit; and
4. *Rosa hybrida* 'KORflusamea' exhibits a large flower size; and
5. *Rosa hybrida* 'KORflusamea' exhibits a yellow flower color, at anthesis; and
6. *Rosa hybrida* 'KORflusamea' exhibits dark green, glossy foliage; and
7. *Rosa hybrida* 'KORflusamea' exhibits very good disease resistance.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORflusamea', taken from plants of three years of age.

DETAILED BOTANICAL DESCRIPTION

The following is a detailed botanical description of a new and distinct variety of *Rosa hybrida* known as 'KORflusamea', based upon observations of plants of three years of age growing in October of 2014 at a nursery in Jackson County, Oreg.

Those skilled in the art will appreciate that certain characteristics will vary with older or, conversely, with younger plants. 'KORflusamea' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2001 edition except where common terms of color are used.

A botanical description of 'KORflusamea' and comparisons with other varieties of *Rosa hybrida* are provided below.

General plant description:

*Growth rate.*—Moderately vigorous.

*Growth habit.*—Upright.

*Mature dimensions.*—Approximately 150 cm tall and 75 cm wide.

*Cold hardiness.*—To date, the variety has been grown successfully in USDA Hardiness Zones 5 through 9.

*Propagation.*—Grafting and stem cuttings.

*Disease resistance.*—Very good resistance to powdery mildew (*Sphaerotheca pannosa*) and blackspot (*Diplocarpon rosae*) diseases under normal growing conditions in Jackson County, Oreg.

Root system:

*Type.*—Fibrous root system with many root hairs.

*Branching.*—Freely branched.

*Density.*—Moderately dense rooting.

*Distribution.*—Roots distributed uniformly throughout the soil profile, from shallow to deep.

Stems:

*Stem color.*—Immature stems are Yellow-Green Group 146C; mature stems are also Yellow-Green Group 146C.

*Intonations.*—Intonations of Greyed-Purple Group 183C are present on immature wood.

*Stem surface texture.*—The surfaces of both immature and mature stems are smooth.

*Prickles.*—Incidence — Present on abaxial leaf surfaces only; not observed on stems. Size — Average length is 1 to 3 mm. Mature prickle color — Yellow-Green Group 145C. Anthocyanin — Greyed-Purple Group 183B present on distal ends of prickles. Shape — Deeply concave. Texture — Smooth.

Leaves:

*Arrangement.*—Imparipinnate compound leaves; mature axillary leaves consisting of 7 leaflets.

*Attachment.*—Petiolate.

*Dimensions.*—155 to 180 mm long and 100 to 110 mm wide.

*Abundance.*—Average.

*Stipules.*—Size — 20 mm long and 6 mm wide. Stipule color — Yellow-Green Group 144A; Yellow-Green Group 145C on the midrib. Anthocyanin — Greyed-Purple Group 183B; present on apices and stipitate glands. Stipitate glands — Abundant on margins. Margins — Glandular toothed. Texture — Glabrous. Apex — Apiculate. Base — Winged.

*Petiole.*—Length — Average 30 to 40 mm. Diameter — Average 1 to 2 mm. Petiole color, adaxial surface — Yellow-Green Group 144A. Petiole color, abaxial surface — Yellow-Green Group 144B. Margins — Entire, with limited numbers of stipitate glands present. Anthocyanin — Greyed-Purple Group 183B. Prickles — Up to two small prickles present on the abaxial surface. Stipitate glands — Limited number present on margins. Texture — Glabrous.

*Rachis.*—Length — Average 20 to 30 mm. Diameter — Average 1 to 2 mm. Color — Yellow-Green Group 146B. Anthocyanin — Greyed-Purple Group 183B, present on stipitate glands, points of leaf attachment, and distal ends of prickles. Margins — Entire, with limited numbers of stipitate glands present. Prickles — A few small prickles underneath. Stipitate glands — Limited numbers of stipitate glands on margins.

*Leaflets.*—Quantity — Normally 7 leaflets on normal leaves in middle of the stem. Dimensions — Average size of the terminal leaflet is 55 to 60 mm long and 35 to 40 mm wide. Shape — Elliptical. Apex — Acute. Base — Obtuse. Margins — Serrated. Texture, adaxial surface — Glossy and leathery. Texture, abaxial surface — Matte and leathery. Pubescence — Glabrous. Juvenile foliage color, adaxial surface — Yellow-Green Group 144A. Juvenile foliage color, abaxial surface — Yellow-Green Group 144A. Mature foliage color, abaxial surface — Yellow-Green Group 147A. Mature foliage color, abaxial surface — Yellow-Green Group 147B. Anthocyanin intonation — Greyed-Purple Group 183B. Present on margins and midrib of juvenile foliage. Venation — Reticulate.

*Petiolule*. —Dimensions — 4 mm long and 1.5 mm in diameter. Petiolule color, adaxial surface — Yellow-Green Group 146B. Petiolule color, abaxial surface — Yellow-Green Group 146C. Prickles — None present. Texture, adaxial surface — Smooth and glabrous. Texture, abaxial surface — Smooth and slightly pubescent, with stipitate glands. Margin — Occasionally with stipitate glands present along margins.

Inflorescence:

*Inflorescence type.*—Panicle.

*Blooming habit.*—Recurrent.

*Quantity of flowers.*—1 to 4, on average.

*Size.*—20 cm tall and 15 cm wide, on average.

*Peduncle.*—Surface — Lacking fine hairs and stipitate glands. Length — 20 to 120 mm average length. Diameter — 3.0 to 4.5 mm average diameter. Color — Yellow-Green Group 146C. Strength — Strong.

Bud:

*Bud form.*—Short. Pointed ovoid.

*Size.*—Upon opening, 25 to 35 mm in length from base of receptacle to distal end of bud and 20 to 25 mm diameter at its widest point.

*Color, as sepals first unfold.*—Yellow-Orange Group 19A, 19B, and 19C with intonations of Red Group 53B.

*Color when one-quarter open, upper surface of petal.*—Marginal zone — Yellow Group 9C. Middle zone — Yellow Group 9B. Basal zone — Yellow Group 9A.

*Color when one-quarter open, lower surface of petal.*—Marginal zone — Yellow-Orange Group 15D. Middle zone — Yellow-Orange Group 16B. Basal zone — Yellow Group 9B.

*Color of outermost petals.*—Marginal zone — Yellow Group 11D. Middle zone — Yellow Group 11D. Basal zone — Yellow Group 12C. Anthocyanin — Intonations of Red Group 53C.

Flower:

*Pedicel.*—Surface — Limited numbers of fine hairs and abundant stipitate glands present. Length — 55 to 80 mm, on average. Diameter — 2 to 3 mm, on average. Color — Yellow-Green Group 146C. Intonations — Greyed-Red Group 182A. Strength — Somewhat strong. Texture — Papillate.

*Sepals.*—Color, adaxial surface — Yellow-Green Group 148C. Color, abaxial surface — Yellow-Green Group 144A. Intonations — Greyed-Purple 183C. Size — 22 to 30 mm long and 10 mm wide, on average. Shape — Weak foliaceous appendages on 3 of the 5 sepals. Apex — Apiculate. Base — Flat at union with receptacle. Quantity — Five. Texture, adaxial surface — Hoary. Texture, abaxial surface — Leathery. Margins — Entire. Stipitate glands — Limited number of stipitate glands present on margins.

*Corolla.*—Corolla habit — Very Double. General shape of corolla — Rosette. Shape of corolla when viewed from the side — Upon opening, upper portion — Flattened convex. Upon opening, lower portion — Flat. Open flower, upper portion — Flattened convex. Open flower, lower portion — Concave. Aspect — Flowers held upright. Dimensions — Large for a floribunda rose. When open, the average flower diameter is 80 to 100 mm and the average flower height is 40 to 50 mm. Fragrance — Light. Duration — On the plant 5 days. Senesced petals clinging. Petals — Petal Arrangement — Not formal. Petal Count — Approximately 55 to 60 petals under normal conditions. Petal Reflex — Petals are strongly reflexed. Reflex occurs one by one. Petal Margin — Retuse and emarginate, as observed. Petal Shape — Obcordate. Apex — Retuse and emarginate. Base — Cuneate. Dimensions — Approximately 35 to 50 mm long and 25 to 50 mm wide. Texture, inner surface — Smooth. Texture, outer surface — Smooth. Color, upon opening — Outermost petals, outer surface — Marginal zone — Yellow-Orange Group 18A. Middle zone — Yellow-Orange Group 16B. Basal zone — Yellow Group 12A. Outermost petals, inner surface — Marginal zone — Yellow-Orange Group 14D. Middle zone — Yellow-Orange Group 14C. Basal zone — Yellow Group 12B. Innermost petals, outer surface — Marginal zone — Yellow-Orange Group 18A. Middle zone — Yellow-Orange Group 19A. Basal zone — Yellow Group 13B. Innermost petals, inner surface — Marginal zone — Yellow-Orange Group 14C. Middle zone — Yellow Group 13B. Basal zone — Yellow Group 12A. Color, petal base — No distinctive coloration at petal base observed. Color after opening — Outermost petals, outer surface — Marginal zone — Yellow-Orange Group 18C. Middle zone — Yellow Group 11B. Basal zone — Yellow Group 10B. Outermost petals, inner surface — Marginal zone — Yellow-Orange Group 14D. Middle zone — Yellow Group 12B. Basal zone — Yellow Group 3A. Innermost petals, outer surface — Marginal zone — Yellow Group 11B. Middle zone — Yellow Group 11B. Basal zone — Yellow Group 8B. Innermost petals, inner surface — Marginal zone — Yellow Group 6D. Middle zone — Yellow Group 6C. Basal zone — Yellow Group 6C. Color, petal base — No distinctive coloration at petal base observed. General Tonality — On open flower Yellow Group 12C. No change in the general tonality at the end of the 4th day. Afterwards, general tonality is Yellow Group 3D. Petaloids — Quantity — Approximately 25 to 30 petaloids per flower. Dimensions — Approximately 10 to 20 mm long and 8 to 20 mm wide. Color, inner surface — Yellow Group 10B. Color, outer surface — Yellow Group 10B. Texture, inner surface — Smooth. Texture, outer surface — Smooth. Margins — Variable; ruffled and emarginate petaloid margins observed. Shape — Most commonly emarginated with many petaloids highly irregular. Apex — Emarginate. Base — Attenuate.

Reproductive organs:

*Stamens.*—Quantity — Approximately 120, on average, and regularly arranged around the styles. Anthers — Shape — Reniform. Dimensions — 1.5 mm long and 1 mm wide, on average. Color — Yellow-Orange Group 18B. Pollen — Generally present. Pollen Color — Greyed-Orange Group N163D. Filaments — Color — Yellow Group 2A. Length — 7 mm.

*Pistils.*—Quantity — Approximately 100 present. Stigmas — Location — Slightly superior in position to anthers. Color — Yellow Group 13B. Styles — Length — Approximately 8 mm long. Color — Yellow Group 4C with intonations of Red Group 52A. Intonations — Red Group 45B.

*Receptacle.*—Shape — Funnel-shaped. Dimensions — Approximately 5 to 7 mm high and 8 to 10 mm wide. Surface — Glaucous, with thin, fine hairs present. Color — Yellow-Green Group 145A with intonations of Greyed-Red Group 182A occasionally present. Texture — Smooth.

Hips and seed formation: Not observed to date.

COMPARISONS WITH THE PARENTS

The new rose plant may be distinguished from its seed parent, *Rosa hybrida* 'KORkinteral', by the following combination of characteristics:

1. 'KORkinteral' has an amber yellow flower color, whereas 'KORflusamea' has a yellow flower color.
2. 'KORkinteral' has semi-glossy foliage, whereas the 'KORflusamea' has glossy foliage.

The new rose plant may be distinguished from its pollen parent, *Rosa hybrida* 'KORfluco', by the following combination of characteristics:

1. 'INTERfluco' has a double corolla habit, whereas 'KORflusamea' has a very double corolla habit.
2. 'INTERfluco' has average disease resistance, whereas 'KORflusamea' has very good disease resistance.

COMPARISONS WITH SIMILAR *ROSA HYBRIDA* CULTIVARS KNOWN TO THE INVENTOR

For a comparison, several physical characteristics of the rose variety 'KORgeleflo', a rose variety from the same inventor described and illustrated in U.S. Plant Pat. No. 21,467 and filed on Aug. 12, 2009, are compared to 'KORflusamea' in Chart 1.

CHART 1

| Characteristic | 'KORflusamea' | 'KORgeleflo' |
|---|---|---|
| Average petal count under normal conditions. | 55 to 60 petals. | 40 to 45 petals. |
| Average open flower diameter. | 80 to 100 mm. | 65 to 75 mm. |
| Average leaf size. | 155 to 180 mm long and 100 to 110 mm wide. | 100 mm long and 65 mm wide. |

That which is claimed:

1. A new and distinct variety of rose plant named 'KORflusamea', as described and illustrated herein.

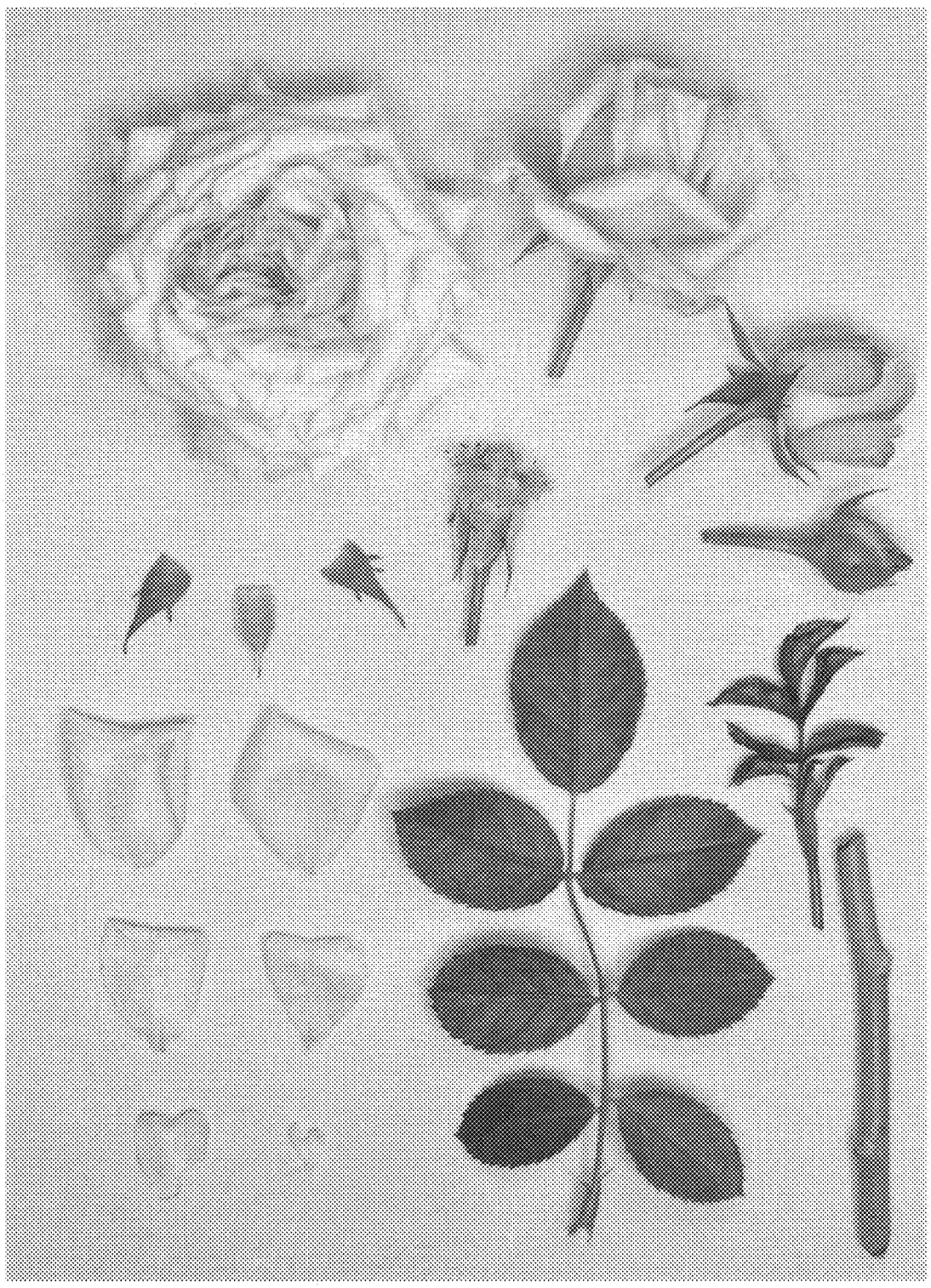

* * * * *